United States Patent [19]
Yamada et al.

[11] Patent Number: 5,242,996
[45] Date of Patent: Sep. 7, 1993

[54] MODIFIED EPOXY RESINS HAVING ACETYLENICALLY UNSATURATED FUNCTIONS

[75] Inventors: Mitsuo Yamada, Suita; Kei Aoki, Ikoma; Ryuzo Mizuguchi, Yawata, all of Japan

[73] Assignee: Nippon Paint Co., Ltd., Osaka, Japan

[21] Appl. No.: 704,154

[22] Filed: May 22, 1991

[30] Foreign Application Priority Data

May 24, 1990 [JP] Japan .................. 2-134594
Sep. 19, 1990 [JP] Japan .................. 2-250924

[51] Int. Cl.$^5$ ............. C08G 59/22; C08G 59/06; C08G 59/22; C07D 303/22
[52] U.S. Cl. ............................ 525/502; 525/529; 525/922; 526/247; 526/251; 526/252; 526/255; 526/273; 526/285; 528/99; 528/101; 528/393; 549/555; 549/557; 549/559; 549/560; 549/515; 549/516; 549/517; 560/9; 560/17; 560/52; 560/55; 560/61; 560/81; 560/95; 560/101; 560/201; 568/32; 568/34; 568/333; 568/631; 568/635; 568/636; 568/637; 568/639; 568/640; 568/641; 568/645; 568/646; 568/649; 568/654; 568/657; 568/673; 568/674
[58] Field of Search ............... 528/99, 101, 393; 525/502, 529, 922; 526/247, 251, 252, 255, 273, 285; 549/555, 557, 559, 560; 560/9, 17, 52, 55, 61, 81, 95, 101, 201; 568/32, 34, 333, 631, 635-637, 639-641, 645-646, 649, 654, 657, 673, 674

[56] References Cited

U.S. PATENT DOCUMENTS

| | | | |
|---|---|---|---|
| 2,792,381 | 5/1957 | Shokal et al. | 526/285 |
| 2,864,804 | 12/1958 | Shokal et al. | 526/319 |
| 2,946,825 | 7/1960 | Monroe et al. | 549/555 |
| 2,986,569 | 5/1961 | Monroe et al. | 549/560 |
| 3,301,743 | 1/1967 | Fekete et al. | 525/531 |
| 3,377,406 | 4/1968 | Newey et al. | 525/529 |
| 3,432,478 | 3/1969 | May | 525/531 |
| 4,371,676 | 2/1983 | Hoene | 526/285 |
| 4,579,959 | 4/1986 | Massingill | 526/273 |
| 4,916,203 | 4/1990 | Pigneri et al. | 525/502 |

*Primary Examiner*—Frederick Krass
*Attorney, Agent, or Firm*—Millen, White, Zelano, & Branigan

[57] ABSTRACT

A modified epoxy resin or compound of the formula:

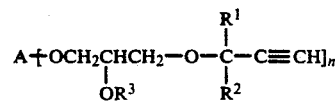

wherein A is the backbone reside of a glycidyl ether epoxy resin with removal of the glycidyloxy groups; $R^1$ and $R^2$ are independently a hydrogen atom or $C_1$-$C_{12}$ alkyl; $R^3$ is a glycidyl group; and n is an integer of greater than 1. A method for producing the modified epoxy resin is also disclosed.

16 Claims, No Drawings

MODIFIED EPOXY RESINS HAVING ACETYLENICALLY UNSATURATED FUNCTIONS

BACKGROUND OF THE INVENTION

This invention relates to modified epoxy resins or compounds having acetylenically unsaturated functions. These resins or compounds may be used in a nonemanating resinous composition capable of curing through different curing mechanisms appropriate to the different functional groups.

It has been known that certain compounds having acetylenically unsaturated groups such as ethynyl or propynyl group may be polymerized into a conjugated diene polymer. Because of their unique polymerization mechanism and the unique electrical and physical properties of their polymers, such compounds are attracting a great interest as a component for producing self-curable, nonemanating resinous compositions. Japanese Patent Kokai No. 108213/89, for example, discloses a propargyl ether of cresol novolac resin as one of such compounds.

The present invention provides a novel class of epoxy-based modified resins having a plurality of acetylenically unsaturated functions in the molecule.

SUMMARY OF THE INVENTION

According to one aspect of the present invention, there is provided a resin or compound having the formula:

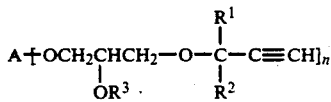

wherein, A is the backbone residue of a glycidyl ether or ester type epoxy resin or compound with removal of the terminal glycidyloxy groups, $R^1$ and $R^2$ are independently hydrogen atom or $C_1$-$C_{12}$ alkyl, $R^3$ is a hydrogen atom or glycidyl group, and n is an integer of greater than 1.

According to another aspect of the present invention, there is provided a method for modifying a glycidyl ether or ester type epoxy resin or compound which comprises reacting a resin or compound having a plurality of terminal glycidyloxy groups with an acetylenic alcohol of the formula:

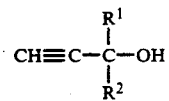

wherein $R^1$ and $R^2$ are as defined, to obtain a corresponding resin or compound having a plurality of terminal groups of the formula:

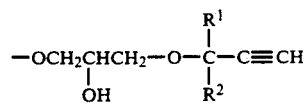

wherein $R^1$ and $R^2$ are as defined.

According to a further aspect of the present invention, there is provided a method for modifying a glycidyl ether or ester type epoxy resin or compound which comprises the steps of:

(a) reacting a resin or compound having a plurality of terminal glycidyloxy groups with an acetylenic alcohol of the formula:

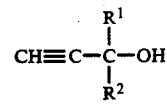

wherein $R^1$ and $R^2$ are as defined, to obtain a corresponding resin or compound having a plurality of terminal groups of the formula:

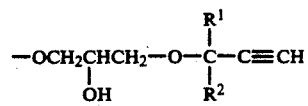

wherein $R^1$ and $R^2$ are as defined;

(b) reacting the product of step (a) with epichlorohydrin or glycerol-1,3-dichlorhydrin and then with an alkali to obtain a corresponding resin or compound having a plurality of terminal groups of the formula:

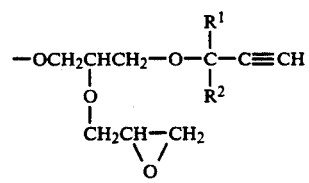

wherein $R^1$ and $R^2$ are as defined.

DETAILED DISCUSSION

The resin or compound of the present invention is characterized by possessing a plurality of terminal groups of the formula:

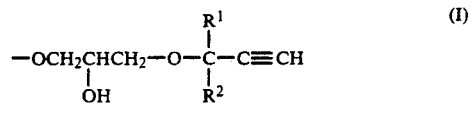

or,

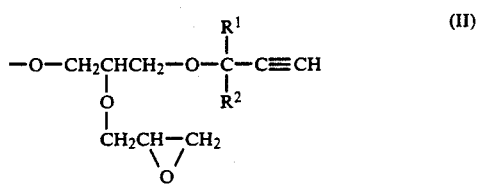

instead of terminal glycidyloxy groups possessed by convention epoxy resins or compounds.

Starting from such conventional epoxy resins or compounds, the overall steps for obtaining the desired products include the following reactions:

Step (a)

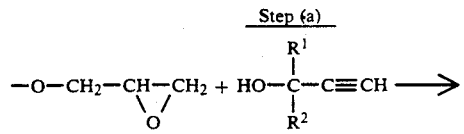

-continued
Step (a)

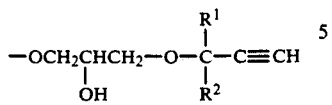

Typical starting materials which may be used herein include bisphenol type epoxy resins such as bisphenol A epoxy resin, bisphenol S epoxy resin, bisphenol F epoxy resin and halogen-substituted bisphenol epoxy resin. The term "bisphenol" as used herein include those compounds in which two phenolic molecules are coupled together by a bridge such as direct bond, —$CH_2$—, —$C(CH_3)_2$—, —$C(CF_3)_2$—, —O— —CO—, —S—, —$SO_2$— and the like. Bisphenol epoxy resins are produced, as is well-known, by reacting bisphenols with epichlorohydrin in the presence of an alkali. Diglycidyl ethers of bisphenols are preferably used.

Novolac epoxy resin may also be used as well.

Another class of epoxy resins or compounds comprises diglycidyl ethers of glycols such as 1,4-butanediol, 1,6-hexanediol, neopentyl glycol, hydrogenated bisphenol A, polyethylene glycol, polypropylene glycol, polytetramethylene glycol, alkylene oxide-adducts of bisphenols and the like.

A further class of epoxy resins or compounds comprises diglycidyl esters of dicarboxylic acids such as oxalic acid, succinic acid, adipic acid, hexahydrophthalic acid, 4-methylhexahydrophthalic acid, tetrahydrophthalic acid, phthalic acid, isophthalic acid, terephthalic acid and the like.

Acetylenic alcohols used in step (a) include propargyl alcohol and its α-mono- and α,α-di-$C_1$-$C_{12}$, preparably $C_1$-$C_4$ alkyl derivatives. Propargyl alcohol is preferred.

The reaction may be carried out in the presence of a basic catalyst such as tertiary amines, quaternary ammonium salts or alkali metal hydroxides either in an inert solvent or without using the solvent. An excess of acetylenic alcohol may be used as a diluent. A reaction temperature ranging between 80° C. and 180° C. may be employed.

The reaction product may be purified by a conventional technique such as fractionation distillation and used as a component of nonemanating resinous compositions, or they may be subjected to the steps (b) and (c) below to introduce an epoxy function.

Steps (b) and (c)

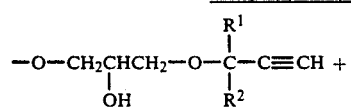

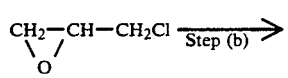

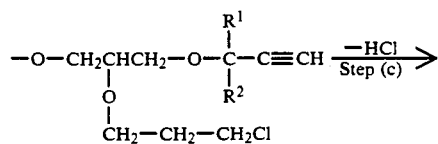

-continued
Steps (b) and (c)

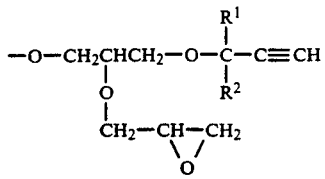

Steps (b) and (c) may be performed either sequentially or simultaneously.

In the sequential process, the product of step (a) is reacted with epichlorohydrin or glycerol-1,3-dichlorohydrin in the presence of a Lewis acid catalyst such as boron trifluoride or its complex, stannic chloride and the like and then with an alkali such as sodium hydroxide, sodium carbonate, barium hydroxide and the like. It is preferable to use epichlorohydrin or glycerol-1,3-dichlorohydrin in excess, for example, about 1.5 to times on the equivalent basis.

In the simultaneous process, the product of step (a) is rected with an excess of epiclorohydrin in the presence of an alkali such as sodium hydroxide and a phase transfer catalyst or tertiary amine or quaternary ammonium base. Typical examples of phase transfer catalyst include methyltrioctylammonium chloride, methyltridecylammonium chloride, tetramethylammonium chloride and tetrabutylammonium bromide, and examples of quarternary ammonium base include benzyltrimethylammonium hydroxide.

An excess, for example, about 2.5 to about 10 times on the equivalent basis of epichlorolhydrin serves to absorb hydrogen chloride produced as a reaction by-product and is converted into glycerol-1,3-dichlorohydrine.

In the both processes, the reaction may be carried out in an inert solvent such as hydrocarbon solvents, ethers and ketones at a temperature from 40° C. to the boiling point of the solvent used.

After removing the solvent, the reaction product may be purified by a conventional technique although crude products containing a small amount of by-products such as chlorohydrin ethers produced in step (b) or hydrolysate of the product of step (c) may be tolerated.

The resins or compounds thus prepared may be polymerized with a metallic catalyst or initiator, or by irradiating with actinic radiations such as UV radiation, gamma radiation or electron beam radiation. They are, therefore, useful as stock materials of resins used in paints, electric and electronic components, structural materials and nonlinear optical materials where nonemanating cure is desired in the finished products.

The invention is illustrated by the following examples wherein all parts and percents are by weight unless otherwise specified.

EXAMPLE 1

A flask equipped with a stirrer, thermometer, nitrogen gas tube and reflux condenser was charged with 475 g of a bisphenol A epoxy resin having an epoxy equivalent of 170, 280 g of propargyl alcohol and 3.075 g of tetrabutylammonium chloride. The mixture was allowed to react by heating at 120° C. until the epoxy equivalent measured by the HCl-dioxane titration method was greater than 15,000. After the reaction, the product was evaporated in vacuo to remove unreacted propargyl alcohol and then poured in 3 liter of methanol with stirring. After standing at room temperature methanol was removed to give a viscous resin having a number average molecular weight as determined by the GPC method of 500.

The structure of the product was identified by the IR spectrum and $^1$H-NMR.

IR: 3300 cm$^{-1}$, 2100 cm$^{-1}$ (CH≡C—); 1610 cm$^{-1}$, 1510 cm$^{-1}$ (Phe); 1110 cm$^{-1}$ (—O—).

$^1$H-NMR (δ, ppm): 2.5 (—C≡CH).

EXAMPLE 2

A flask as used in Example 1 was charged with 500 g of a bisphenol A epoxy resin having an epoxy equivalent of 450, 138 g of polycaprolactone polyol having a number average molecular weight of 500, 3.18 g of benzyldimethylamine and 160 g of xylene. The mixture was allowed to react by heating at 150° C. until an epoxy equivalent of 1200 was reached.

After the above chain-extending reaction, the product was further reacted with 80 g of propargyl alcohol until the epoxy function disappeared. The reaction mixture was then evaporated in vacuo to remove unreacted propargyl alcohol and xylene, and poured in 3 liter of methanol with stirring. After standing at room temperature, methanol was removed to give a viscous resin having a number average molecular weight of 2600 as determined by the GPC method.

IR: 3300 cm$^{-1}$, 2100 cm$^{-1}$ (CH≡C—), 1110 cm$^{-1}$ (—O—).

$^1$H-NMR (δ, ppm): 2.5 (—C≡CH).

EXAMPLE 3

Analogous to Example 1, 475 g 1,4-diglycidyloxybutane was reacted with 528 g of propargyl alcohol to give 1,4-bis(3-propargyloxy-2-hydroxypropyl) oxybutane.

IR: 3300 cm$^{-1}$, 2100 cm$^{-1}$ (CH≡C—).

$^1$H-NMR (δ, ppm): 2.5 (—C≡CH).

EXAMPLE 4

Analogous to Example 1, 475 g of a cresol novolac epoxy resin having an epoxy equivalent of 220 (Toto Kasei K.K., YDCN-704) was reacted with 240 g of propargyl alcohol. A resin having a number average molecular weight of 2500 was obtained.

IR: 3300 cm$^{-1}$, 2100 cm$^{-1}$ (CH≡C—), 1110 cm$^{-1}$ (—O—).

$^1$H-NMR (δ, ppm): 2.5 (—C≡CH).

EXAMPLE 5

Analogous to Example 1, 475 g of a bisphenol A epoxy resin having an epoxy equivalent of 450 was reacted with 180 g of 2-methyl-3-butyne-2-ol to give a resin having a number average molecular weight of 1200.

IR: 3300 cm$^{-1}$, 2100 cm$^{-1}$ (CH≡C—), 1110 cm$^{-1}$ (—O—).

$^1$H-NMR (δ, ppm): 2.5 (—C≡CH).

EXAMPLE 6

2,2-Bis[4-(3-propargyloxy-2-glycidyloxypropyloxy)-phenyl]propane

A flask equipped with a stirrer, thermometer, nitrogen gas tube and reflux condenser was charged with 170.0 g of bis(4-glycidyloxyphenyl)propane, 224.0 g of propargyl alcohol and 1.0 g of benzyldimethylamine. The mixture was allowed to react by heating at 115° C. until no epoxide function was detected by the HCl-dioxane titration method. After the reaction, unreacted propargyl alcohol was removed from the reaction mixture by evaporation in vacuo.

To the mixture were added 740.0 g of epichlorohydrin and 4.0 g of tetramethylammonium chloride. To the mixture heated at 50° C., 86.0 g of 50% aqueous solution of sodium hydroxide was added dropwise over 2 hours. Then reaction was continued for additional 4 hours while removing water as an azeotropic mixture with epichlorohydrin in vacuo. After removing excessive epichlorohydrin, the reaction product was treated with toluene-water mixture to extract sodium chloride by-product in water and the toluene fraction was evaporated in vacuo to remove the solvent. The title compound having an epoxy equivalent of 290 (283 in theory) was obtained in a yield of 90.0% of theory.

IR (cm-1):

CH≡C-(3300, 2100)

CH$_3$-(2900)

—Ph-(1600, 1500)

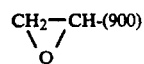-(900)

H-NMR (ppm):

C$\underline{H}_3$-(1.62)

C$\underline{H}$≡C-(2.44)

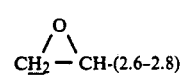-(2.6-2.8)

CH$_2$—CH-(3.20) (epoxide)

≡C—C$\underline{H}_2$-(4.19)

Ph—$\underline{H}$(6.80-7.13)

EXAMPLE 7

Bis[4-(3-propargyloxy-2-glycidyloxypropyloxy)-phenyl]methane

A flask as used in Example 6 was charged with 155.0 g of bis(4-glycidyloxyphenyl)methane, 224.0 g of propargyl alcohol and 1.0 g of tetramethylammonium chloride. The mixture was allowed to react by heating at 115° C. until no epoxide function was detected by the HCl-dioxane titration method. After the reaction, unreacted propargyl alcohol was removed from the reaction mixture by evaporation in vacuo.

To the mixture was added 0.5 g of boron trifluoride-diethyl ether complex and the temperature raised to 80° C. To this was added dropwise 103.0 g of epichlorohydrin and the reaction was continued until the epoxide function disappeared. Then 160.0 g of 50% aqueous solution of sodium hydroxide was added to the cooled reaction mixture and allowed to react for additional 6 hours at 30° C. After the reaction, excessive sodium hydroxide was neutralized and the product was washed with deionized water repeatedly to remove sodium chloride by-product. The title compound having an epoxy equivalent of 280 was obtained in a yield of 80.0% of theory.

IR (cm$^{-1}$):

CH≡C-(3300, 2100)

—Ph-(1600, 1510)

CH$_2$—CH-(910)
\ /
O

H-NMR (ppm):

C<u>H</u>≡C-(2.46)

C<u>H$_2$</u>—CH-(2.6–28)
\ /
O

CH$_2$—C<u>H</u>-(3.21)
\ /
O

≡C—C<u>H$_2$</u>-(4.19)

Ph—<u>H</u>(6.81–7.15)

EXAMPLE 8

Bis[4-(3-propargyloxy-2-glycidyloxypropyloxy)-phenyl]sulfone

A flask as used in Example 6 was charged with 180.0 g of bis(4-glycidyloxyphenyl)sulfone, 224.0 g of propargyl alcohol and 1.0 g of tetramethylammonium chloride. The mixture was allowed to react by heating at 115° C. until no epoxide function was detected by the HCl-dioxane titration method. After the reaction unreacted propargyl alcohol was removed from the reaction mixture by evaporation in vacuo.

To the mixture were added 40.0 g of epichlorohydrine and 4.0 g of tetramethylammonium chloride. To the mixture heated at 50° C., 86.0 g of 50% aqueous solution of sodium hydroxide was added dropwise over 2 hours. Then reaction was continued for additional 4 hours while removing water as an azeotropic mixture with epichlorohydrin in vacuo. After removing excessive epichlorohydrin, the reaction product was treated with toluene-water mixture to extract sodium chloride by-product in water and the toluene fraction was evaporated in vacuo to remove the solvent.

The title compound having an epoxy equivalent of 300 was obtained in a yield of 92.0% of theory.

IR (cm$^{-1}$):

CH≡CH-(3300, 2100)

CH$_2$—CH-(900)
\ /
O

H-NMR (ppm)

C<u>H</u>≡CH-(2.44)

C<u>H$_2$</u>—CH-(2.6–2.8)
\ /
O

CH$_2$—C<u>H</u>-(3.20)
\ /
O

≡C—C<u>H$_2$</u>-(4.19)

Ph—<u>H</u>(6.80–7.14)

Analogous to Example 6, the following compounds were produced.

EXAMPLE 9

4,4'-Bis(3-propargyloxy-2-glycidyloxypropyloxy)benzophenone

Epoxy equivalent: 278
Yield: 92.4%

IR (cm$^{-1}$):

CH≡C-(3300, 2100)

—Ph-(1600, 1500)

CH$_2$—CH-(910)
\ /
O

H-NMR (ppm):

C<u>H</u>≡C-(2.45)

C<u>H$_2$</u>—CH-(2.6–2.8)
\ /
O

Ph—<u>H</u>(6.6–7.8)

EXAMPLE 10

4,4'-Bis(3-propargyloxy-2-glycidyloxypropyloxy)-biphenyl

Epoxy equivalent: 266
Yield: 86.5%

IR (cm$^{-1}$):

CH≡C-(3300, 2100)

—Ph-(1600, 1500)

CH$_2$—CH-(900)
\ /
O

H-NMR (ppm):

C<u>H</u>≡C-(2.45)

C<u>H$_2$</u>—CH-(2.6–2.8)
\ /
O

Ph—<u>H</u>(6.6–7.8)

EXAMPLE 11

2,2-Bis[4-(3-propargyloxy-2-glycidyloxypropyloxy)-2-methylphenyl]propane

Epoxy equivalent: 312

Yield: 88.3%

IR (cm-1):

CH≡C-(3300, 2100)

—Ph-(1600, 1500)

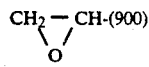CH₂—CH-(900) / O

H-NMR (ppm):

—C<u>H</u>₃(1.70)

C<u>H</u>≡C-(2.44)

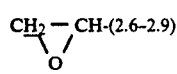CH₂—CH-(2.6-2.9) / O

Ph—<u>H</u>(6.6-7.8)

EXAMPLE 12

1,4-bis(3-propargyloxy-2-glycidyloxypropyloxy)butane

Epoxy equivalent: 165
Yield: 77.2%

CH≡C-(3300, 2100)

—CH₂-(2850)

CH₂—CH-(900) / O

H-NMR (ppm):

—C<u>H</u>₂-(1.62)

C<u>H</u>≡C-(2.44)

CH₂—CH-(2.6-2.8) / O

EXAMPLE 13

1,6-Bis(3-propargyloxy-2-glycidyloxypropyloxy)hexane

Epoxy equivalent: 186
Yield: 80.0%

IR (cm⁻¹):

CH≡C-(3300, 2100)

—CH₂-(2850)

CH₂—CH-(910) / O

H-NMR (ppm)

—C<u>H</u>₂-(1.62)

Ph—<u>H</u>(6.6-7.8)

EXAMPLE 14

2,2-Bis[4-(3-propargyloxy-2-glycidyloxypropyloxy)-3,5-dibromophenyl]propane

Epoxy equivalent: 450
Yield: 88.1%

IR (cm⁻¹):

CH≡C-(3300, 2100)

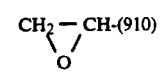CH₂—CH-(910) / O

H-NMR (ppm):

C<u>H</u>≡C-(2.44)

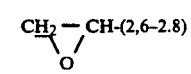CH₂—CH-(2,6-2.8) / O

Ph—<u>H</u>(6.6-7.8)

EXAMPLE 15

2,2-Bis[4-(3-propargyloxy-2-glycidyloxypropyloxy)-phenyl]-1,1,1,3,3,3-hexafluoropropane Epoxy equivalent: 345
Yield: 91.0%

IR (cm-1):

CH≡C-(3300, 2100)

—PH-(1600, 1500)

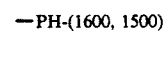CH₂—CH-(910) / O

H-NMR (ppm):

C<u>H</u>≡C-(2.44)

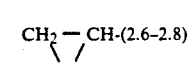CH₂—CH-(2.6-2.8) / O

Ph—<u>H</u>(6.6-7.8)

What is claimed is:

1. A compound of the formula:

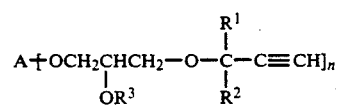

$$A\text{-}[\text{OCH}_2\text{CHCH}_2\text{-O-}\underset{R^2}{\overset{R^1}{\underset{|}{\overset{|}{C}}}}\text{-C}\equiv\text{CH}]_n$$
$$\quad\quad\quad\quad|\quad\quad\quad$$
$$\quad\quad\quad\text{OR}^3\quad\quad\quad$$

wherein A is the residue of a glycidyl ether epoxy resin, said epoxy resin having a plurality of terminal glycidyloxy groups, which results upon removal of the terminal glycidyloxy groups; $R^1$ and $R^2$ are independently a hydrogen atom or $C_1\text{-}C_{12}$ alkyl; $R^3$ is a glycidyl group; and n is an integer of greater than 1.

2. The compound of claim 1, wherein $R^1$ and $R^2$ are independently a hydrogen atom or $C_1\text{-}C_4$ alkyl.

3. The compound of claim 2, wherein said residue A is derived from a bisphenol epoxy resin.

4. The compound of claim 2, wherein said residue A is derived from a novolac epoxy resin.

5. The compound of claim 2, wherein said residue A is derived from a glycol-diglycidyl ether epoxy resin.

6. The compound of claim 1, wherein A represents two phenyl groups which are coupled together by a direct bond or a —CH$_2$—, —C(CH$_3$)$_2$—, —C(CF$_3$)$_2$—, —O—, —CO—, —S— or —SO$_2$— group.

7. The compound of claim 6, wherein R$^1$ and R$^2$ are hydrogen atoms.

8. The compound of claim 6, wherein R$^1$ and R$^2$ are C$_1$-C$_{12}$ alkyl groups.

9. The compound of claim 6, said compound being 2,2-bis[4-(3)-propargyloxy-2-glycidyloxypropyloxy)-phenyl]propane.

10. A method of modifying an epoxy resin having a plurality of terminal glycidyloxy groups which comprises the steps of:

(a) reacting said epoxy resin with an acetylenic alcohol of the formula:

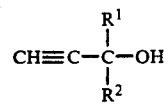

wherein R$^1$ and R$^2$ are independently a hydrogen atom or C$_1$-C$_{12}$ alkyl; and subsequently, (b) reacting the product of step (a) with epichlorohydrin or glycerol-1,3-dichlorohydrin; and (c) reacting the product of step (b) with an alkali.

11. The method of claim 10, wherein R$^1$ and R$^2$ are independently a hydrogen atom or C$_1$-C$_4$ alkyl.

12. The method of claim 10, wherein said step (b) is carried out in the presence of a Lewis acid catalyst and is followed by said step (c).

13. The method of claim 10, wherein said step (b) and said step (c) are carried out simultaneously using an excess of epichlorohydrin in the presence of a phase transfer catalyst, a tertiary amine or a quaternary ammonium hydroxide together with said alkali.

14. The method of claim 10, wherein said epoxy resin is a bisphenol epoxy resin.

15. The method of claim 10, wherein said epoxy resin is a glycol-diglycidyl ether epoxy resin.

16. The method of claim 10, wherein said epoxy resin is a novolac epoxy resin.

* * * * *